(12) United States Patent
Browne et al.

(10) Patent No.: US 7,620,211 B2
(45) Date of Patent: Nov. 17, 2009

(54) METHOD AND APPARATUS FOR QUANTIFYING VISUAL SHOWTHROUGH OF PRINTED IMAGES ON THE REVERSE OF PLANAR OBJECTS

(75) Inventors: Richard Walker Browne, Wilmington, DE (US); Robert V. Canning, Jr., Bear, DE (US); Michael H. Evans, Newark, DE (US); Robert William Johnson, Kennett Square, PA (US); Barry Rubin, Glen Mills, PA (US); Douglas Ray Stilwell, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 810 days.

(21) Appl. No.: 10/549,781

(22) PCT Filed: Apr. 7, 2004

(86) PCT No.: PCT/US2004/010710

§ 371 (c)(1), (2), (4) Date: Sep. 19, 2005

(87) PCT Pub. No.: WO2004/092874

PCT Pub. Date: Oct. 28, 2004

(65) Prior Publication Data

US 2006/0181749 A1  Aug. 17, 2006

Related U.S. Application Data

(60) Provisional application No. 60/461,201, filed on Apr. 7, 2003.

(51) Int. Cl.
*G06K 9/00* (2006.01)
*G01N 21/00* (2006.01)

(52) U.S. Cl. .................................. 382/112; 356/435

(58) Field of Classification Search ............... 382/141, 382/112; 356/435
See application file for complete search history.

(56) References Cited

U.S. PATENT DOCUMENTS

| 3,455,637 | A |  | 7/1969 | Howard |
|---|---|---|---|---|
| 3,827,808 | A |  | 8/1974 | Cho |
| 4,019,819 | A | * | 4/1977 | Lodzinski ............ 356/73 |

(Continued)

FOREIGN PATENT DOCUMENTS

GB    2 065 301    6/1981

(Continued)

OTHER PUBLICATIONS

TAPPI Method T519, 2002.

(Continued)

*Primary Examiner*—Wenpeng Chen

(57) ABSTRACT

An image analysis method to quantify visual showthrough of printed images on the reverse face of planar objects, such as paper. An illumination level is set using a white reference object. A white reference image is stored in a computer memory. An image of a planar object having a printed image on the reverse face is stored in a computer memory. A pixel by pixel ratio of the two images is calculated and a mean value of the ratios is calculated to characterize the visual showthrough. The measurements are substantially independent of both the illumination level and image shading.

18 Claims, 13 Drawing Sheets

U.S. PATENT DOCUMENTS

| | | | |
|---|---|---|---|
| 4,159,876 A * | 7/1979 | Egan et al. | 356/312 |
| 4,455,090 A * | 6/1984 | Roberts | 356/448 |
| 4,529,318 A * | 7/1985 | Curl | 356/430 |
| 4,656,663 A | 4/1987 | Jansson et al. | |
| 5,082,529 A | 1/1992 | Burk | |
| 5,113,454 A | 5/1992 | Marcantonio et al. | |
| 5,793,486 A | 8/1998 | Gordon et al. | |
| 5,999,636 A | 12/1999 | Juang | |
| 6,081,612 A | 6/2000 | Gutkowicz-Krusin et al. | |
| 6,437,862 B1 * | 8/2002 | Miyazaki et al. | 356/237.2 |
| 6,438,256 B1 | 8/2002 | Rubin et al. | |
| 7,145,697 B1 * | 12/2006 | Sharma et al. | 358/3.26 |
| 2002/0039181 A1 * | 4/2002 | Shakespeare et al. | 356/73.1 |
| 2004/0021869 A1 | 2/2004 | Shakespeare et al. | |

FOREIGN PATENT DOCUMENTS

WO    WO 98/20326    5/1998

OTHER PUBLICATIONS

Tony Ho, Applying Digital Image Technology to Pulp and Paper, Canadian Conference on Electrical and Computer Engineering, 1993, pp. 1139-1143, vol. 2.

Tappi, Opacity of Paper (15/d Geometry, Illuminant A/2 69% Reflectance Backing and Paper Backing, 2001.

International Search Report Dated Apr. 29, 2005, International Application No. PCT/US04/10710, International Filing Date: Apr. 7, 2004.

* cited by examiner

METHOD AND APPARATUS FOR QUANTIFYING VISUAL SHOWTHROUGH OF PRINTED IMAGES ON THE REVERSE OF PLANAR OBJECTS

CROSS REFERENCE TO RELATED APPLICATIONS

This application claims the benefit of U.S. Provisional Application No. 60/461,201, filed Apr. 7, 2003, which is incorporated by reference in its entirety.

FIELD OF THE INVENTION

This invention relates to an apparatus for measuring showthrough of a printed image from the reverse side of a planar object and methods therefor. More particularly, this invention relates to an apparatus which measures the optical reflectance of the front surface to measure showthrough and methods therefor.

BACKGROUND OF THE INVENTION

For planar printing substrates, such as paper products, there is a need for hiding power and visual appearance uniformity. Optical opacifiers, such as titanium dioxide ($TiO_2$), are used to provide these attributes. A highly uniform front surface appearance is desired in these products, even when there is printing on the reverse surface of the product. The degree to which images printed on the reverse surface can be seen when the front surface is illuminated and viewed is known as "showthrough". It is well known that the thickness and the inherent opacity of the product, as well as the penetration depth of the ink printed on the reverse surface, affect the degree of showthrough.

Showthrough may be evaluated by trained human operators who make subjective ratings of the surface appearance based on visual observations of the front surface under controlled lighting conditions. Opacity measuring instruments, known as opacimeters, have been traditionally utilized to quantify the degree of showthrough within a single small region on the surface. A standard measurement protocol, using such an instrument, is set forth in Technical Association of the Pulp and Paper Industry (TAPPI) standard T-425 om 01, entitled "Opacity of Paper (15/d Geometry, Illuminant A/2 Degrees, 89% Reflectance Backing and Paper Backing)". Measurements made with such instruments, however, measure a very small portion of the overall area of a sample sheet and are thus ill-suited to provide a representative measure of showthrough, particularly when a patterned, image, or indicia, is printed on the reverse side of the product. An automated imaging system and method, such as that of the present invention, should provide a more representative measure of showthrough.

A method for quantifying visual appearance uniformity of planar surfaces of opaque objects is described in U.S. Pat. No. 6,438,256 (assigned to the assignee of the present invention). This method, however, does not address the need for assessing the visual showthrough of printed images on the reverse side of a sheet of paper.

SUMMARY OF THE INVENTION

The invention relates to a method for measuring the degree to which a printed image on a first side of a sheet is visible when illuminating and viewing a second side of the sheet, the method comprising:

a) creating a calibration image of a reference object containing no image by illuminating the reference object at an initial illumination level;

b) determining an average gray level of the reference object and adjusting the illumination level to achieve a predetermined average gray level;

c) illuminating the sheet at an illumination level the same as that used to create the calibration image and creating an image of the sheet;

d) measuring the ratio of the pixel intensities of the image of the sheet with the corresponding pixel intensities of the calibration image; and e) calculating a mean value of the ratios of the pixel intensities.

The invention further relates to an image analysis method for characterizing the showthrough of a printed image on the reverse surface of a substantially planar sample object having a reflective front surface, by measuring the optical reflectance of the front surface with a lens and a photodetector array, the method comprising the steps of:

(a) creating a frame-averaged dark current image representing the response of the photodetector array in the absence of light;

(b) uniformly illuminating, with a diffuse light source, the front surface of a reference object, said reference object having no image on its reverse, and creating a calibration image of the reference object, comprising the steps of;
  (1) illuminating the front surface of the reference object with the diffuse light source, the output of the light source being set to an initial illumination output level;
  (2) creating a frame-averaged image of the front surface of the reference object;
  (3) determining the average gray level in the image of the reference object created in step(b)(2);
  (4) adjusting the illumination level by adjusting the output of the light source and repeating steps (2) and (3) until the average light level reflected by the front surface of the reference object causes an average gray level in the image of step (2) to be within a predetermined range of a predetermined value within the dynamic range of the analog to digital converter, thereby establishing a predetermined illumination level;
  (5) creating a frame-averaged reference image of the front surface of the reference object;
  (6) creating a dark-current corrected calibration image of the reference object by subtracting the frame-averaged dark current image of step (a) from the frame-averaged reference image of step (5) on a pixel by pixel basis and storing the resulting image in the memory;

(c) uniformly illuminating, with the diffuse light source at the predetermined illumination level, the front surface of a sample object having a printed image on the reverse surface;

(d) creating a frame-averaged image of the front surface of the sample object;

(e) creating a dark-current-corrected image of the front surface of the sample object by subtracting the frame-averaged dark current image of step (a) from the frame-averaged image of step (d) on a pixel by pixel basis and storing the resulting image in the memory; and (f) analyzing the dark-current-corrected frame-averaged image by calculating the ratio of the image of step (e) with the image of step (b)(6) on a pixel by pixel basis to quantify showthrough.

Still further the invention relates to an apparatus for measuring the degree to which a printed image on a first side of a substantially planar sample object is visible when illuminating and viewing a second side of the substantially planar sample object, the apparatus comprising:

a) a light tight enclosure comprising a sample object holder, an illuminating assembly for diffusely illuminating the sample object, and an imaging assembly, b) a computerized image processing assembly for controlling the illumination level of the sample object created by the illuminating assembly and for receiving images created by the imaging assembly and analyzing those images, wherein (1) the sample object holder comprises a support frame and a support platen for holding the sample object to be measured in a predetermined plane, (2) the illuminating assembly comprises:
  (i) a hemispherical reflector positioned adjacent the sample holder so that the predetermined sample plane corresponds to the equatorial plane of the hemisphere, the hemisphere having a diffusely reflecting interior surface and a polar opening for mounting the imaging assembly,
  (ii) a circular array of light sources positioned above the equatorial plane and arranged to illuminate the diffusely reflecting interior surface of the hemisphere;
  (iii) a photodetector positioned adjacent the array of light sources and oriented to sense the level of light diffusely reflected from the interior surface of the hemisphere;

(3) the imaging assembly comprising:
  (i) a lens,
  (ii) a photodetector array, the lens focusing an image of the object onto the photodetector array, each photodetector in the array creating an electrical signal representative of the light reflected from the front surface of the object, the photodetector array being connected to the computerized image processing assembly.

The method of the present invention is believed to be advantageous in several ways. For each type paper to be characterized the illumination level is set by creating a reference or calibration image utilizing a plurality of unprinted sheets of that type of paper in a stack or pad sufficiently thick so that all of the light that penetrates through the top of the paper stack is reflected or absorbed. Such a stack represents an "optically infinitely thick" stack, and if additional sheets are added to the stack, no change in overall reflectance results. An image of the stack is created and the illumination level is adjusted so that the mean pixel value is within a predetermined narrow range within the overall dynamic range of the analog to digital converter, typically near the upper end of the dynamic range. This insures a sufficiently high signal level from a sample and minimizes effects of system noise.

A feedback control is provided so that the illumination of the sample is stable over the period of time during which the images of a group of samples are being acquired, typically only a few minutes per group of samples. The method also insures that the showthrough measurement is independent of illumination intensity variations over the field of view.

The illumination assembly provides a diffuse source of illumination to the sample sheet being measured, with the illumination intensity being substantially uniform over the area being imaged. A hemispherical dome, coated with a white diffusely reflecting coating is illuminated around its perimeter by a circular array of white light emitting diodes (LEDs).

The images are also corrected for camera photodetector dark current. This substantially removes contributions of the camera dark current from the measured gray level across the image. Since a dark current image may be captured and stored as often as desired, the measurement is effectively insensitive to changes in CCD photodetector dark current which may be related to temperature changes or aging effects in the camera CCD or electronics. The CCD camera utilized is substantially photometrically linear, so that changes in measured pixel intensity directly correlate to changes in surface reflectance.

DETAILED DESCRIPTION OF THE INVENTION

Showthrough Measurement Principles

When evaluating the opacity of printing substrates such as paper or film it is necessary to quantify the visibility of a printed image on the backside of a printed page. A parameter called DuPont™ Showthrough Value™, or DSV™, is a measure of the visibility of a printed image on the backside of a printed page. A DSV™ of zero indicates a completely opaque page, i.e., the presence of printing on the back of the sheet is not detectable. A DSV™ of 100 indicates that the page is completely transparent or that the ink from the printing has bled through the page.

The contribution of ink penetration to print showthrough, called Strike-In, can be calculated by taking the difference between Printed DSV™ and Unprinted DSV™.

Printed DSV™=100 (1−$Ro'/Rinf$)

Unprinted DSV™=100 (1−$Ro/Rinf$)

Strike-In=Printed DSV™−Unprinted DSV™

Where:
  Ro—Reflectance of a single unprinted sheet on a black backing.
  Ro'—Reflectance of a single printed sheet with the print opposite the illuminated side on a black backing.

Rinf—Reflectance of an infinite pad of unprinted sheets. An infinite pad is defined as a pad (or stack) of sufficient thickness such that increasing the thickness does not change the reflectance reading.

The equations for DSV™ contain a term that is a ratio of a single sheet reflectance to a reference reflectance, in this case Rinf. This term is called a contrast ratio and is a measure of the opacity of the sheet. Dividing the single sheet reflectance by a reference reflectance removes the effect of surface reflectivity (also called sheet brightness) from the DSV™ reading. The contrast ratio is subtracted from 1.0 to give a reading that increases with increasing showthrough. A sheet with no showthrough gives a zero DSV™ reading.

Apparatus

Figure 1:
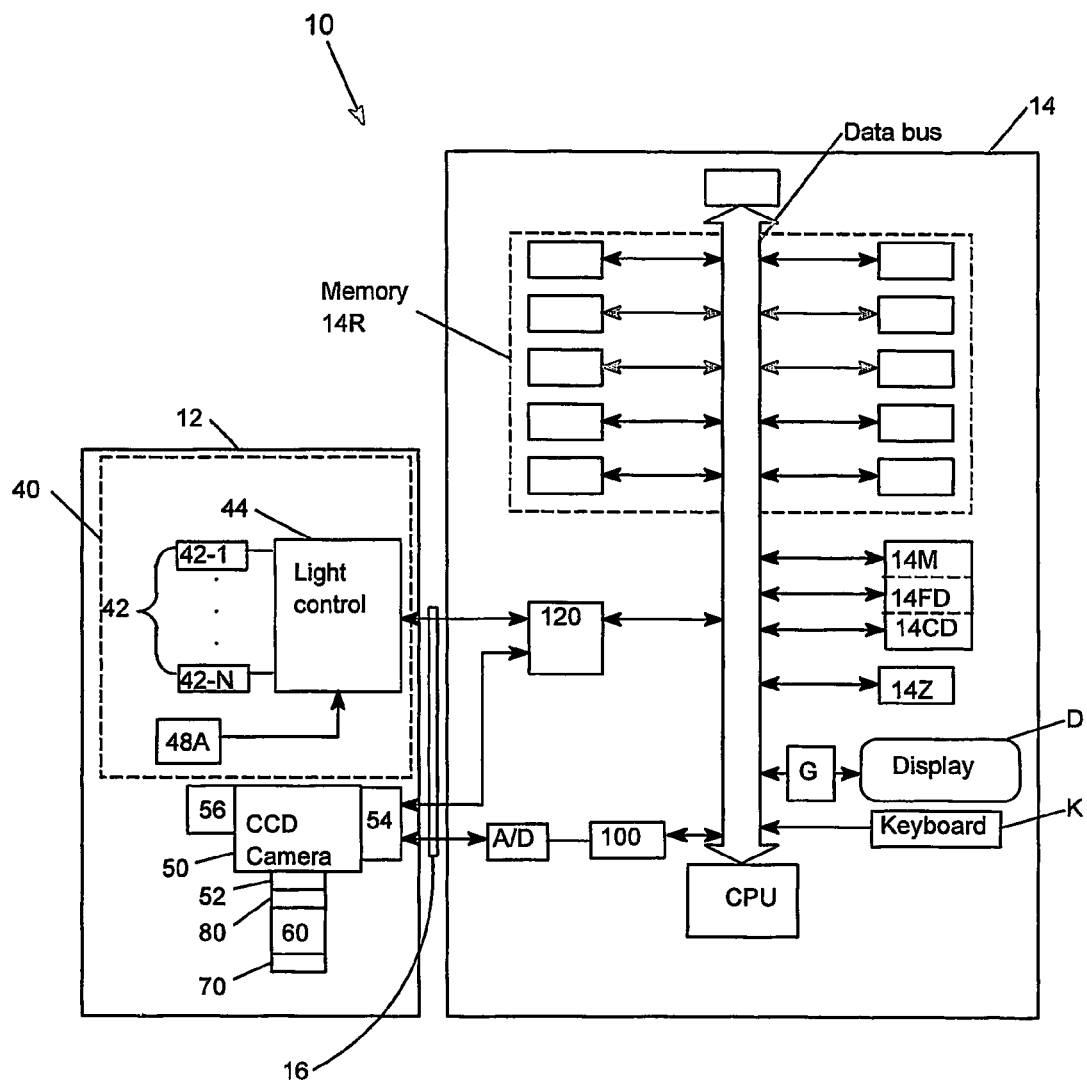
FIG. 1 shows a block diagram of a system for measuring showthrough of an image on a sheet.
Figure 2:
FIG. 2 is a pictorial view of an arrangement for measuring showthrough of an image on a sheet.

The apparatus 10 of the present invention, as seen in FIG. 1, comprises a planar object imaging assembly 12, also referred to as the sample imaging assembly, and an associated computerized image processor (or simply computer) 14. The planar object imaging assembly 12, best seen in FIGS. 2, 3A, 3B, 4, and 5A, comprises a light-tight housing 20 (FIG. 5A) in which are mounted a sample holding fixture 30, an illumination assembly 40, a CCD camera 50, a multi-element lens 60 and an optical filter assembly 70 and an optional photopic filter assembly 80.

Figure 3A:
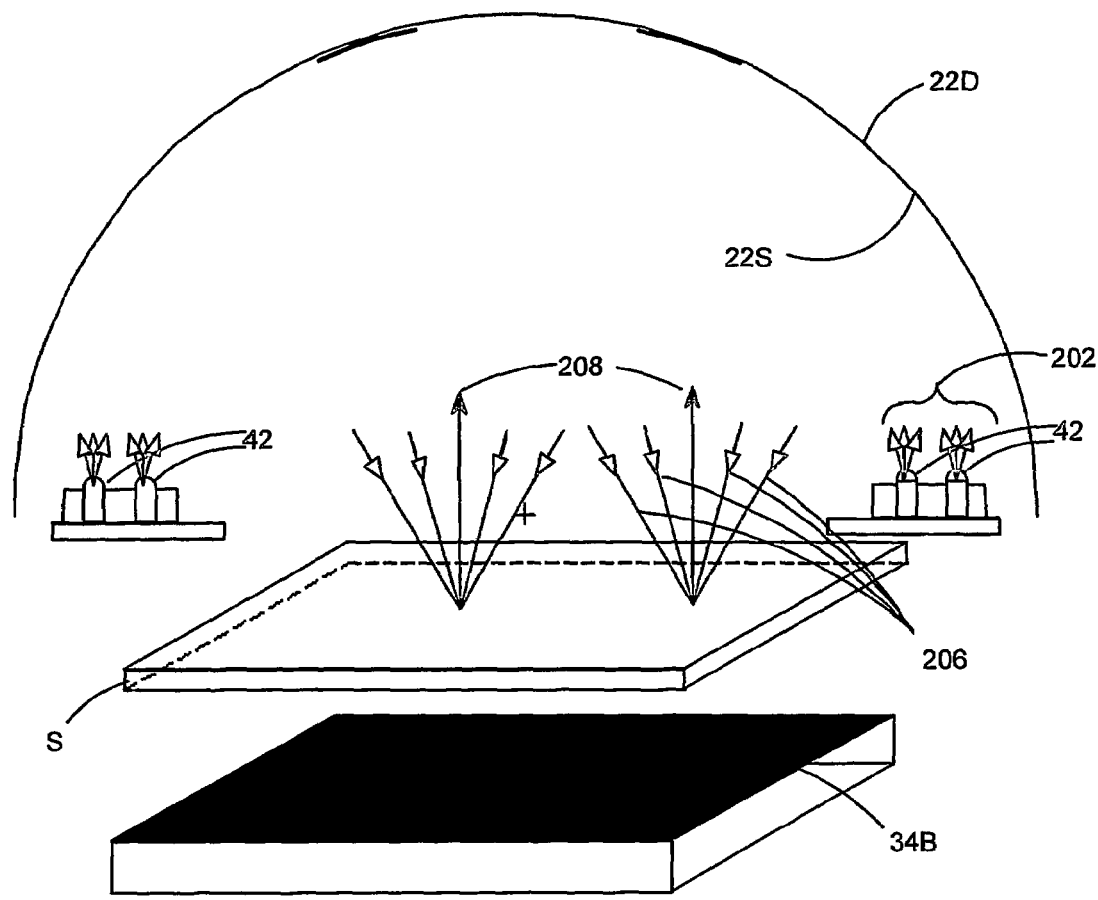
FIG. 3A shows an exploded perspective view of an unprinted sheet illuminated from a first side, the sheet being mounted on a black surface, with the light source in section.
Figure 3B:
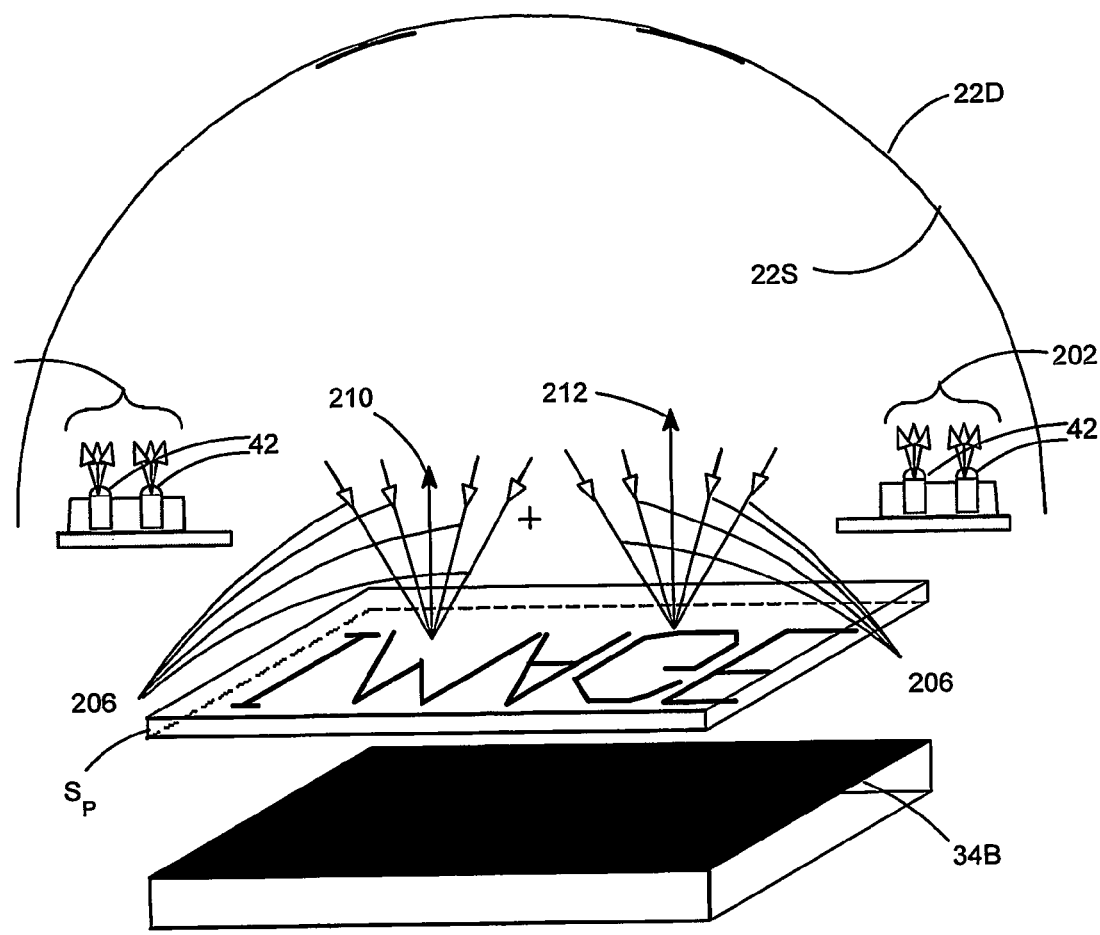
FIG. 3B shows an exploded perspective view of a printed sheet illuminated from a first side, the sheet having a printed image on a second side, the sheet being mounted on a black surface, with the light source shown in section.
Figure 4:
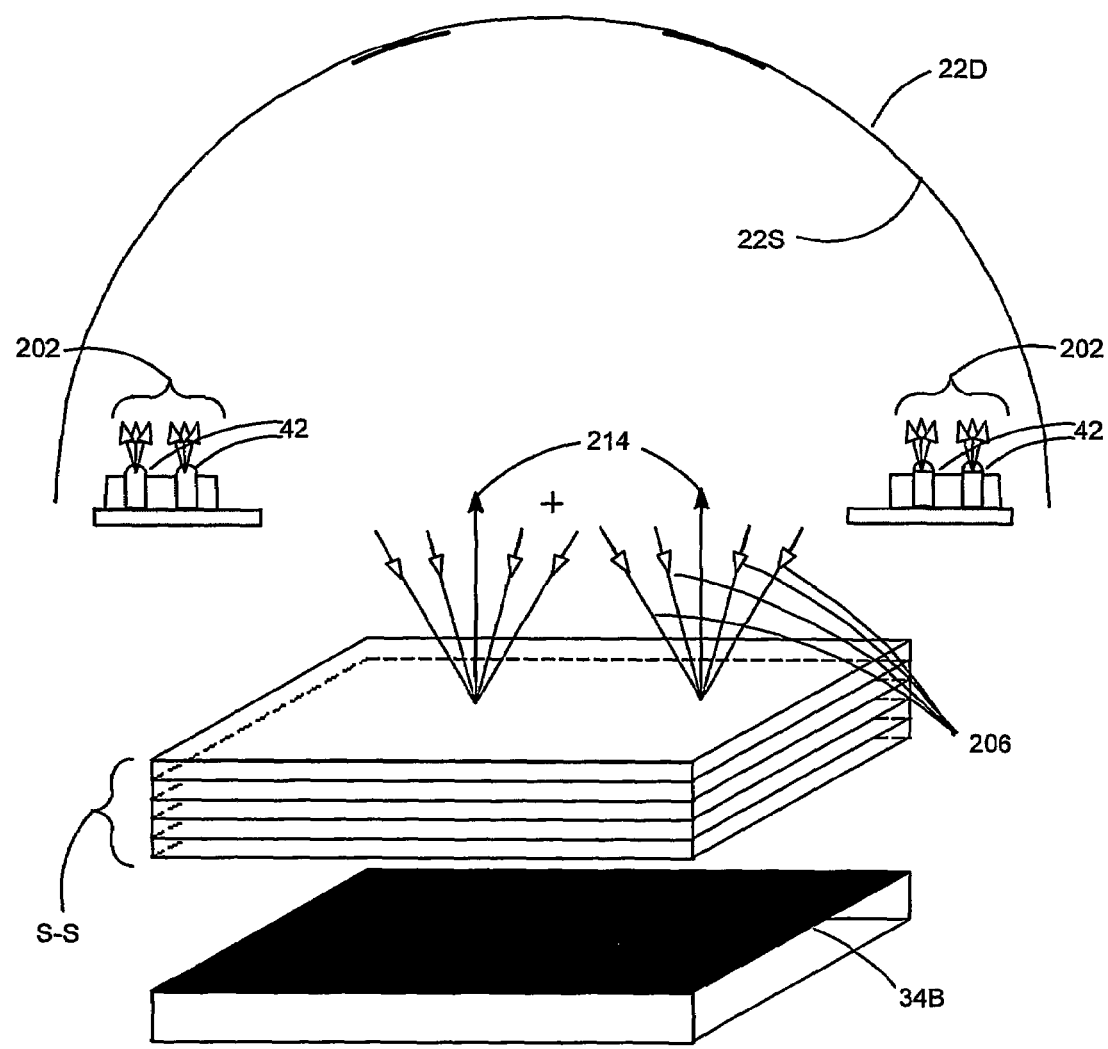
FIG. 4 shows an exploded perspective view of a stack or pad of sheets used for measuring the reflectance of an "infinite pad" of unprinted sheets, with the light source shown in section.
Figure 5A:
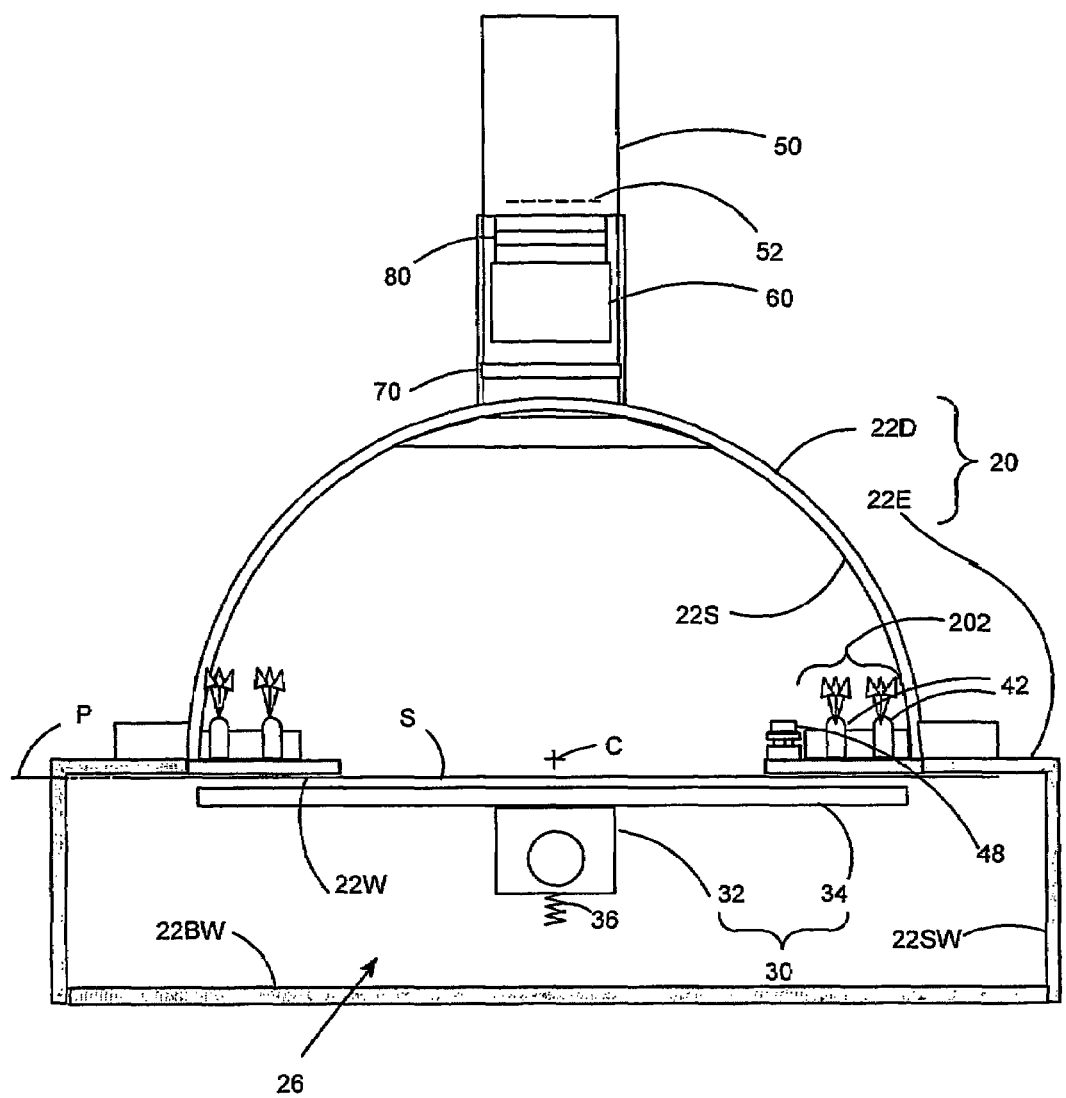
FIG. 5A shows a sectional view of a light source arrangement for illuminating a sheet to be measured.

The housing 20 comprises a generally rectangular enclosure 22E (best seen in FIG. 5A) having a bottom wall 22BW, side wall 22SW, and an interior dividing wall 22W, upon which is mounted a top hemispherical dome 22D (FIGS. 3A, 3B, 4, and 5A). The sample holding fixture 30 comprises a generally planar clamping device 32 that holds a sample S flat in a holding frame 34 in an opening in the interior dividing wall 22W of the housing 20. The clamping device 32 is urged against the frame 34 by a spring 36 (FIG. 5A). The frame 34 defines a sample plane P. The frame 34 has a black upper surface 34B that contacts the sample sheet S, shown in FIGS. 3A, 3B and 4.

Figure 5B:
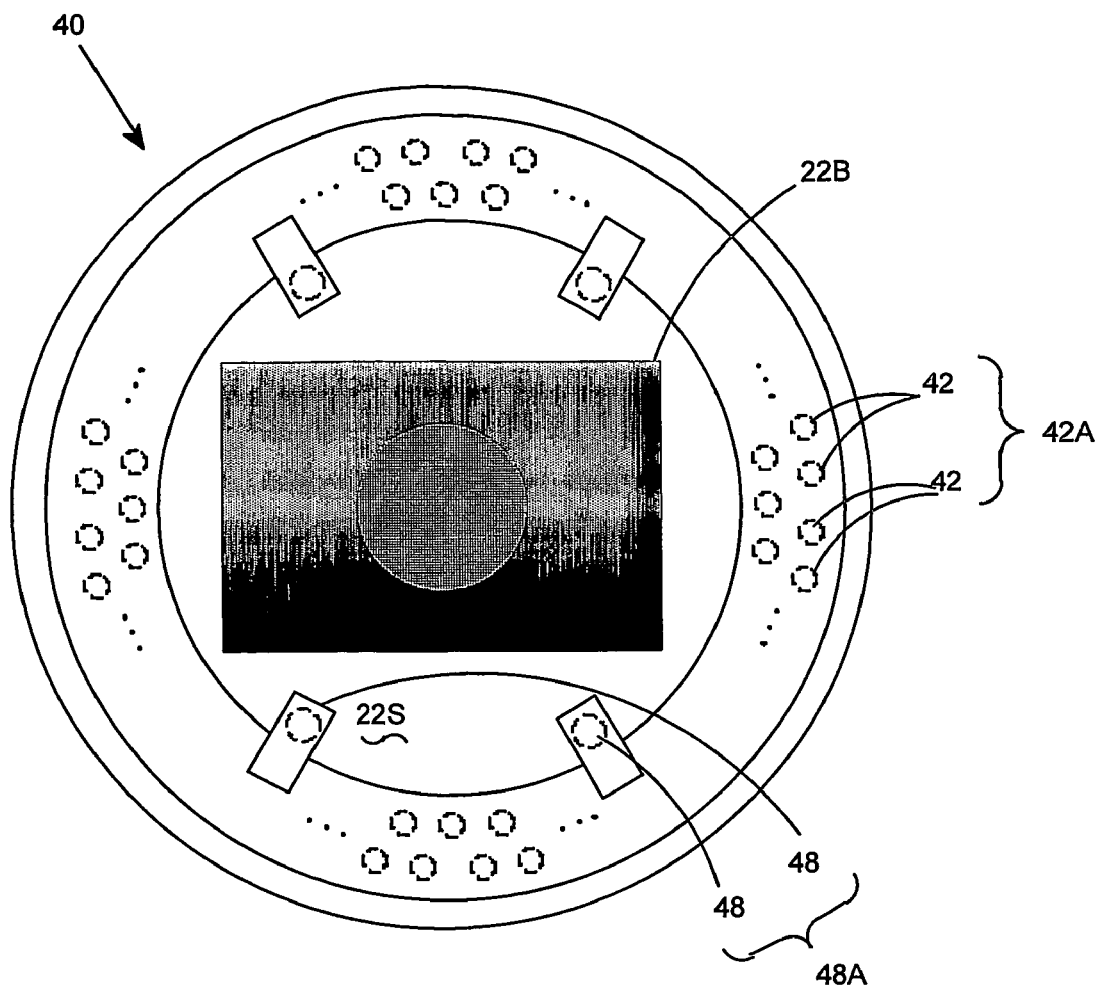
FIG. 5B shows a plan view, looking upward, of the illumination assembly.

As shown in FIG. 5B, the illumination assembly 40, which illuminates the planar sample S, comprises a circular array 42A of light sources 42 mounted within a dome 22D. As shown in FIG. 5A, the light sources 42, which are preferably light emitting diodes, are mounted just above the interior dividing wall 22W, i.e., at the equatorial position of the hemisphere. The inner surface 22S of the hemisphere of the dome 22D is coated with a white diffusely reflecting coating.

FIG. 5B shows a portion 22B of the interior surface of the hemisphere adjacent the polar opening has a substantially non-reflecting region so that specular reflections from the sample sheet S are not imaged by the imaging assembly. The shape of the portion 22B corresponds to the shape of the area of the sample sheet being imaged. This feature insures that only diffusely reflected light is imaged by the camera 50. This becomes particularly important when analyzing planar objects having a glossy surface, since specular reflections from such a glossy surface could cause artifacts in the image and degrade the accuracy of the showthrough measurement.

A plurality of light emitting diodes 42 are positioned above the plane P of the sample S and are symmetrically disposed about the center C of the sample S in a circular array 42A within an annular area adjacent to the perimeter of the hemispherical dome 22D. The annular area typically extends from approximately seventy to approximately ninety percent of the diameter of the hemispherical dome 22D. FIG. 5B depicts several portions of a typical circular array 42A. As seen in FIG. 1, the light emitting diodes 42 are divided into N groups, 42-1 through 42-N, typically twenty-four groups of five LEDs in each group, for a total of one hundred twenty LEDs. Suitable LEDs are manufactured by Nichia and are sold as part number NSPW 500-BS. Each group is wired in series with a current limiting resistor. Each of the groups is then wired in parallel with the other groups and connected to a light level controller 44 such as a current source.

Before the illumination assembly 40 is put into use a voltage verification test is performed. The LEDs are wired together and then low voltage is applied and adjusted until all the lamps begin to turn on.

Typically the turn-on voltage is 11-12 volts DC. If a few lamps turn on before the others, then those lamps are replaced. This insures that all the lamps must turn on evenly and produce substantially uniform light levels. A commercially illumination assembly, available from Advanced Illumination, Inc. of Rochester, Vt., wired as described above, has been found suitable.

Figure 6:
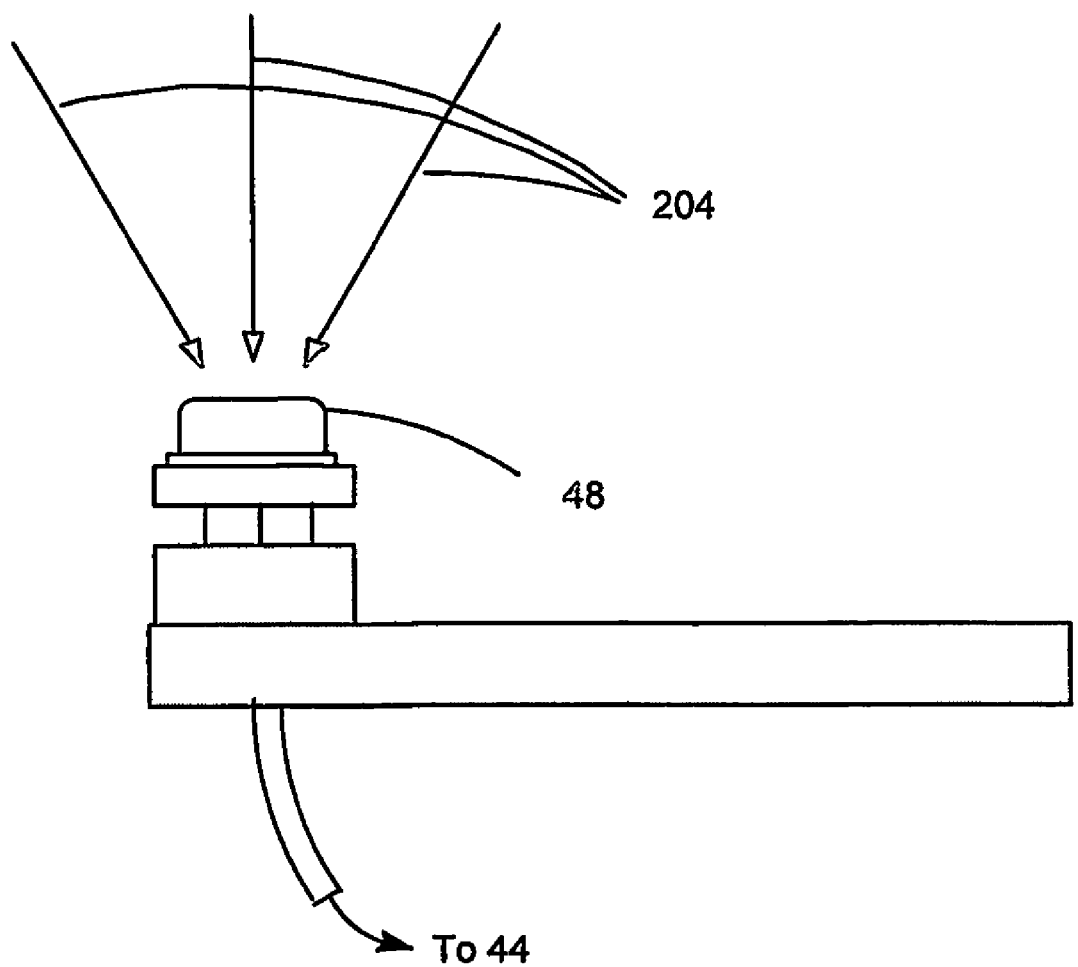
FIG. 6 shows an enlarged view of the photodetector used to control the illumination level.

As seen in FIG. 1, the light level controller 44 is controlled by a control signal from I/O card 120 in the computer 14 and by a photodetector assembly 48A, which may comprise one or more photodetector cells 48, symmetrically arranged (best seen in FIGS. 5A and 5B), such as a photodetector from Advanced Photonix, Inc. of Camarillo, Calif. FIG. 5B shows a photodetector assembly 48A having four photodetector cells 48, but any desired number of cells 48 may be employed. The photodetector 48 monitors the light that has been diffusely reflected from the surface 22S (arrows 204) and provides a feedback signal to the light controller 44 to produce a precise illumination level (see FIG. 6). It should be understood that a small portion of the light incident on each photodetector cell 48 has been reflected from the sample S and re-reflected from the surface 22S one or more times.

The interior wall 22W and the inner surface 22S of the hemispherical dome 22D define a sample illumination chamber 26. The interior surfaces of the walls of the sample illumination chamber 26 are coated with a high reflectivity, diffusely reflecting material, such as a flat white paint, to provide a uniform illumination level to the surface of the sample S. A preferred coating is sold under the trade name Duraflect, a proprietary water resistant and durable white reflectance coating, having a reflectivity at a wavelength of 600 nanometers (nm) of 94-96% and an effective spectral range: 350-1200 nm, available from Labsphere, Inc. of North Sutton, N.H.

The dome 22D has an opening at the top (e.g., at the polar position) to accommodate a camera 50. The camera 50, the multi-element lens 60, and the filter assemblies 70, 80 are mounted on the top of the dome so that the multi-element lens 60 projects an image of the sample plane P onto a CCD photodetector array 52 within the camera 50. The lens 60 is mounted a fixed distance above the sample plane P, in accordance with the focal length of the lens. A suitable lens is a Schneider XNP 1.4/23-0302, CM-120, 23 mm focal length, f1.4, available from Schneider Optics Inc., Hauppauge, N.Y. 11788 as Part #21-010425, which is mounted about 16 centimeters (6.325 inches) above the sample plane P.

The optical filter assembly 70 comprises a commercial haze filter mounted on the front of the lens 60 and the camera 50, and serves primarily to mechanically protect the lens 60. A filter assembly 80 may be used to control the spectral response of the system so that the image analysis method utilizes information in a predetermined spectral region, such as to match the spectral response of the human eye. A filter available from Barr Associates of Wesiford, Mass. as part #0401-3030B has been found satisfactory for such purpose. This filter 80 is typically mounted between the lens 60 and the CCD camera 50. A filter 80 having a maximum transmission of greater than 95 percent, a center wavelength of 555 nm ±5 nm and half-power points of 510 nm (±5 nm) and 610 nm (±5 nm) respectively, results in a system spectral response that approximates the response of the human eye.

The camera 50, such as model KP-MIA video camera, available from Hitachi Denshi America, Ltd. of Woodbury, N.Y., has an associated camera power supply 56. The camera 50 comprises a CCD photodetector array 52 and associated control and interface electronics 54, is mounted vertically with the CCD photodetector array 52 positioned so that the sample plane P is imaged by the lens 60 onto the CCD photodetector. The multi-element lens 60 is typically set with its aperture at about f/8. A field of view of about 7 centimeters by 5 centimeters (2.8 inch×2.0 inch) on the sample S is typically imaged.

Video images generated by the camera 50 are transmitted by a cable 16 to the computerized image processor 14. The video cable may be a 2 meter long camera cable with right angle connector available from Visics Corporation, Wellesley, Mass. as part # VCSL2-2.0-P. The computerized image processor 14 may comprise a Broadax Systems, Inc. (BSI) model PCATXN9-154, 15.4" TFT 1280×1024 SXGA Portable Computer.

This computer comprises a display device D, such as a 15.4 inch TFT 1280×1024 LCD screen with analog-to-digital video signal converter; integrated keyboard with touch pad, built-in speakers, 300 Watt ATX power supply; two 5.25" vertical, two 3.5" horizontal open, one hidden 3.5" drive bays; and wheeled carrying bag w/retractable handle. Standard Configuration Includes an ATX motherboard, an Intel® Pentium-4® 1.8 GHz CPU, Random Access Memory (RAM) 14R comprising 128 MB SDRAM, magnetic storage devices 14M comprising a EIDE 40.0 gigabyte (GB) hard drive, a 1.44 MB floppy drive, a 48X EIDE CD-ROM drive, and a graphics module G comprising a Conversion Board W/Asus GeForce4 MX440-8X V9180Magic 64 MB DDR TVOUT.

Also included are a local area network module LAN, comprising a 3COM #3C905-TX 10/100 BT LAN (PCI), and operating system software such as Microsoft's Windows 2000 Professional®. Peripheral devices include a National Instruments Corp. model PCI 1409 multi-channel monochrome frame grabber 100 (National part number 778200-1), model PCI 6503 digital I/O card 120 (National part number 777690-1), and associated software such as IMAQ Vision for Labview® (part number 778044-1).

For clarity of illustration two types of light rays are shown in FIGS. 3A, 3B and 4. Light rays emitted from a light source or incident upon a sample sheet are shown as arrows having an arrowhead with an open outline. At any given point only three or four arrows are shown. Arrowheads reflecting from a sample sheet are shown as arrows having an arrowhead with a solid outline. FIG. 3A shows an exploded perspective view of an unprinted sample sheet S illuminated from a first side, the sheet being mounted on a black surface 34B. FIG. 3A is exploded for clarity, but as may be appreciated from viewing the sectional view FIG. 5A, the sample sheet S is in direct contact with the black surface 34B. The illuminating dome 22D and the light sources 42 are shown in section. The arrows 202 represent light rays emitted from the light sources 42. After diffusely reflecting from the interior surface 22S of dome 22D, the light arrives at the sample sheet, as depicted by arrows 206. The light rays reflected by the surface of the sample sheet are depicted by arrows 208.

FIG. 3B shows an exploded perspective view of a printed sample sheet $S_p$ illuminated from a first side, the sheet having a printed image (the word "IMAGE" depicted in reverse) on a second side, the sample sheet $S_p$ being mounted on a black surface 34B. The illuminating dome 22D and the light sources 42 are shown in section. The arrows 202 represent light rays emitted from the light sources 42. After diffusely reflecting from the interior surface 22S of dome 22D, the light arrives at the sheet, as depicted by arrows 206. The light reflected by the surface of the sample sheet $S_p$ outside the area of the printed image is depicted by arrows 210. The light reflected by the surface of the sample sheet $S_p$ within the area of the printed image is depicted by arrows 212.

FIG. 4 shows an exploded perspective view of a stack or pad of unprinted sheets S-S used for measuring the reflectance of an "infinite pad" of unprinted sheets. The illuminating dome 22D and the light sources 42 are shown in section. The arrows 202 show the light emitted from the light sources 42. After diffusely reflecting from the interior surface 22S of dome 22D, the light arrives at the surface of the top sheet of the stack S-S, as depicted by arrows 206. The light reflected by the surface of the stack S-S is depicted by arrows 214.

Video images, typically measuring 640 pixels wide by 480 pixels high, are digitized by an eight-bit (256 gray levels) analog to digital (A/D) converter in the frame grabber 100 and are stored in a suitable memory device. Camera voltage levels between 0 volts (pedestal level) and 0.714 volts are digitized to gray levels between 0 and 255.

Dark Signal Correction

The measurement parameter used in the present invention will be substantially independent of light level only when the dark signal is accounted for and the true image signal is measured.

Thus, the procedure for correcting for dark signal is as follows:

Sample the dark signal by blocking the camera lens or turning off the light source. Store the dark signal image (with suitable frame averaging) in a memory buffer of the same size and format as the subsequent reference object or sample images.

After each sample image is digitized, subtract the pixel values of the dark signal image in the memory buffer, pixel by pixel, from the pixel values in the reference object image or the sample image.

Control of Illumination Level

Figure 7:
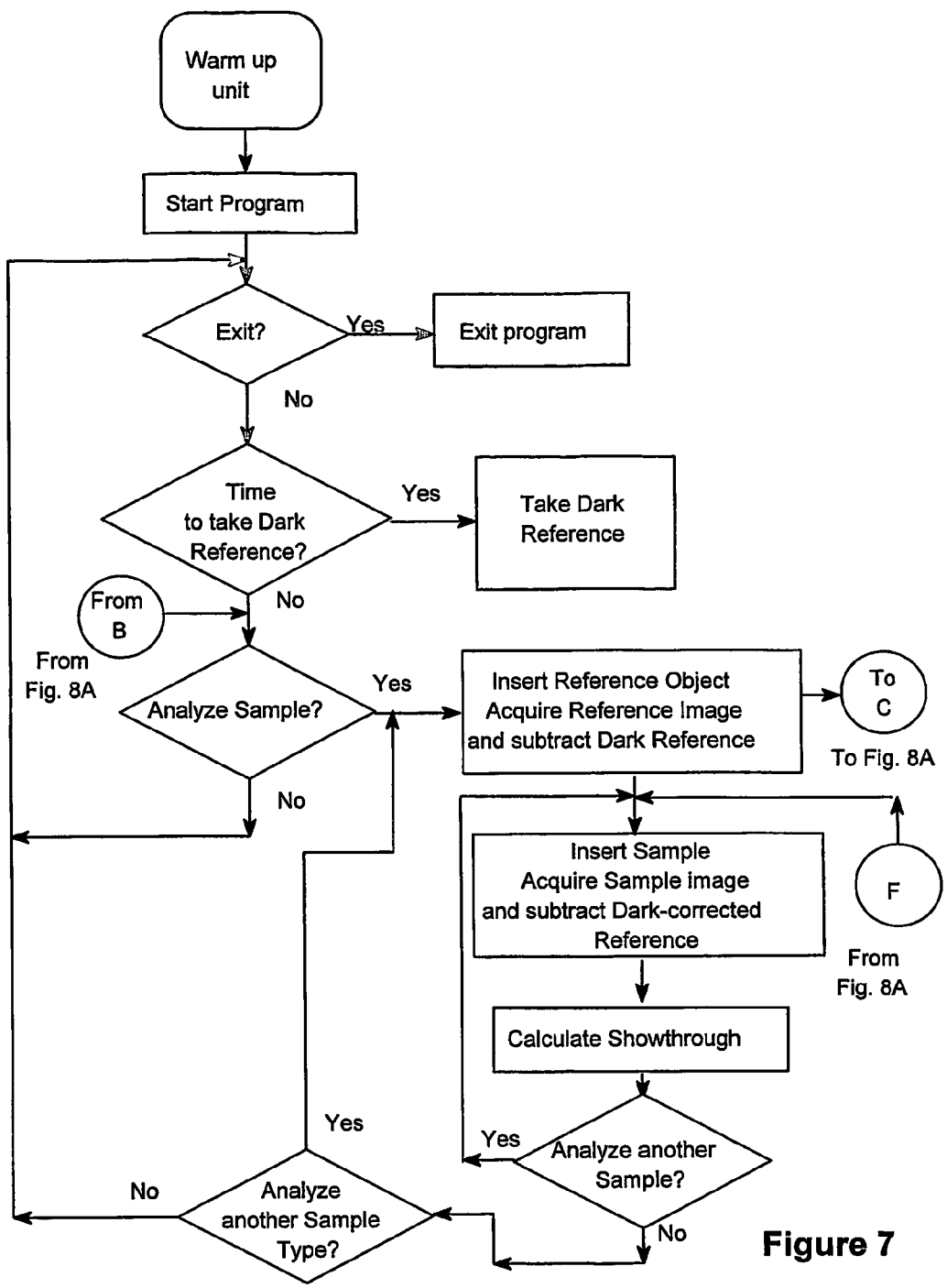
FIG. 7 is a block diagram illustrating the overall method of the present invention.
Figure 8A:
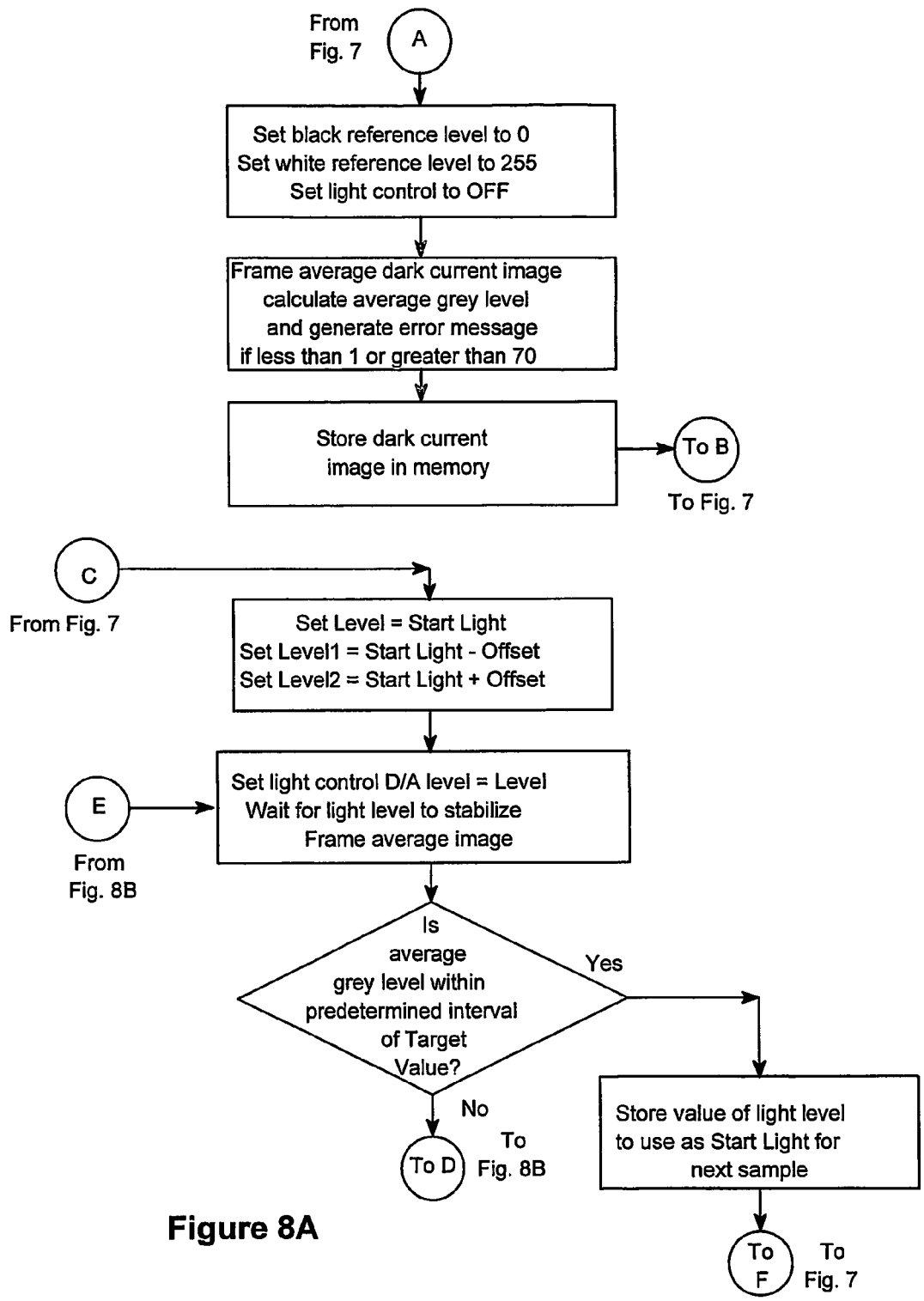
FIGS. 8A and 8B show block diagrams illustrating a method of adjusting the illumination level of the sample.
Figure 8B:
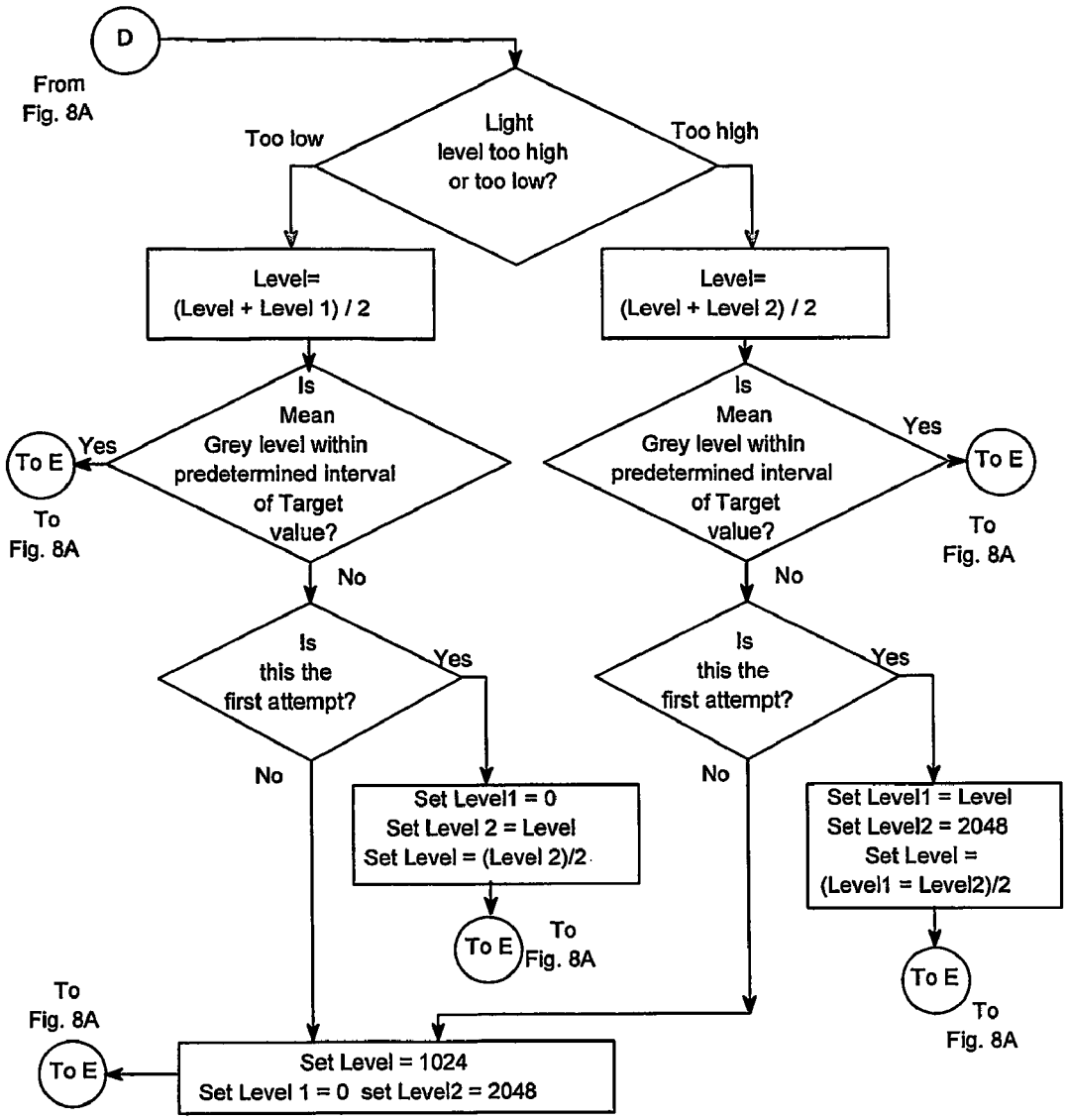

As shown in FIG. 7 and FIGS. 8A and 8B, the computerized image processor 14 is programmed to precisely control the light level illuminating the reference object and the sample sheet S. The surface of the reference object is illuminated with the illumination assembly 40, with he light source being set to an initial output level. A digitized frame-averaged image of the surface of the reference object is created by first imaging the light reflected from the surface onto the photodetector array to create an electrical signal representative of the image. The electrical signal is digitized and frame averaged a predetermined number of times and the frame-averaged representation of the image is stored in the image processor memory 14R. The average gray level in the image is determined and the illumination level of the reference object is adjusted until the average gray level in the image is at a desired level, typically near the upper end of the dynamic range of the analog to digital converter.

As seen in FIGS. 8A and 8B, to accelerate the measurement of a group of samples, each having an associated reference object, the initial illumination level is set by initially setting the light source output level to the level used for the previous reference object. The illumination adjusting step is first performed using a binary search method to set the light source output level within a predetermined range of light levels. If the desired average gray level of the reference object image is not achieved, the illumination adjusting step is then performed using a binary search method to set the light source output level over the full range of light levels.

Analysis Method

With the full voltage range of A/D voltages selected, the illumination system is turned off so that no light reaches the CCD array. The image produced by the photodetector array in the camera in the absence of light, known as the "dark response" or "dark current" image, is digitized a predetermined number of times (typically 64 or 128) and then frame averaged. That is, the corresponding picture elements, or pixels, in each of the images are added and then divided by the number of images digitized to produce an image which represents the average dark current response of the CCD array and its associated electronics. This so called "average dark current" image is stored in memory 14R, such as RAM or in magnetic storage media 14M, for subsequent use.

The average dark current image is stored in memory and subsequently subtracted from each sample image to correct each pixel in the sample image.

For each type of paper, i.e., each set of samples, an "infinite stack" of unprinted sheets is used to establish a predetermined illumination level. (see FIG. 4). This illumination level is automatically set so the camera output voltage to the A/D converter for the "infinite stack" of sheets is such that the average gray level in the image is in a predetermined range, such as the range 200±1. Alternately, the illumination level can be adjusted to provide the highest possible average gray level without camera saturation for each white reference. The digital I/O card 120-computer 14 provides a control signal to the light level controller 44. The illumination level is sensed by the photodetector assembly 48A and the photodetector signal is fed to the light level controller 44 and is compared to the control signal to automatically control the illumination level.

The so called "infinite stack" serves as a reference object with which the subsequently acquired sample images will be compared by calculating the ratio of each corresponding pixel. Each image of the "infinite stack" is frame averaged a predetermined number of times (typically 64) and the dark current frame-averaged image is then subtracted from it on a pixel by pixel basis to produce a "dark current corrected calibration image of the reference object".

Region of Interest

The system of the present invention also has the capability to restrict measurement on a sample to a region of interest (ROI) within the field of view. The ROI is specified by the user interactively through placement of a cursor box, which is displayed superimposed on an image of the sample, that is moved and sized by pressing appropriate keys on the terminal input device to the image processor 14. In the standard analysis method, the entire image is measured.

Operation of the Apparatus

Overall operation of the apparatus is shown in FIG. 7. The user specifies the number of samples (also known as replicates) in a group to be measured. Before a measurement of a first sample is performed, the user is prompted to insert a reference object, also called a white reference, in the instrument. The white reference is a stack of unprinted papers of the same type as the sample papers. The illuminator intensity is set so that the average gray level in the white reference image is at a predetermined level, say 200. This illumination intensity is fixed once for all samples in a group of samples. The light control circuit parameter required to achieve this illumination level is stored for use with all samples that are associated with this white reference. The image of the white reference is acquired at this illumination level, using frame averaging. The previously acquired dark reference image is subtracted, pixel-by-pixel, from the white reference image to create a dark current-corrected calibration image of the reference object.

When analyzing each replicate sample, the illumination level is held at the level used with the white reference by using the stored light control circuit parameter. The sample image is acquired at this illumination level, using frame averaging. The previously acquired dark reference image is subtracted, pixel-by-pixel, from the sample image to create a corrected sample image. Then, for each pixel, the ratio of the corrected sample gray level to the corrected white reference gray level is calculated. These gray level ratio values are then averaged over all pixels to calculate an average gray level ratio R. As discussed previously, the ratio R for an unprinted sheet is equal to Ro/Rinf, while the ratio R' for a printed sheet is equal to R'o/Rinf. The unprinted sheet DuPont™ Showthrough Value™, DSV™, is equal to 100*(1−R) and the printed sheet DuPont™ Showthrough Value™, DSV™, is equal to 100*(1−R').

As shown in FIG. 5B, the photodetector assembly 48A is positioned within the hemispherical reflector 22D and is interfaced to an electronic circuit to control the illumination at a constant level. This optical feedback from the photodetector assembly 48A to the light level controller 44 insures that the illumination level is maintained with a high degree of accuracy for all the samples of a group once a particular setting is made and insures the ability to return to the same illumination level with a high degree of accuracy. This prevents drifting of the illumination level that would adversely affect the showthrough measurement.

In one embodiment, the invention herein can be construed as excluding any element or process step that does not materially affect the basic and novel characteristics of the composition or process. Additionally, the invention can be construed as excluding any element or process step not specified herein.

EXAMPLE

The method of the invention was used to characterize a set of coated groundwood paper samples. Bimonthly printing trials were made using paper supplied by six different paper mills. Samples were printed on the same piece of printing equipment. The same images were printed on paper from all six sources for each monthly production run to facilitate paper quality comparisons.

Figure 9:
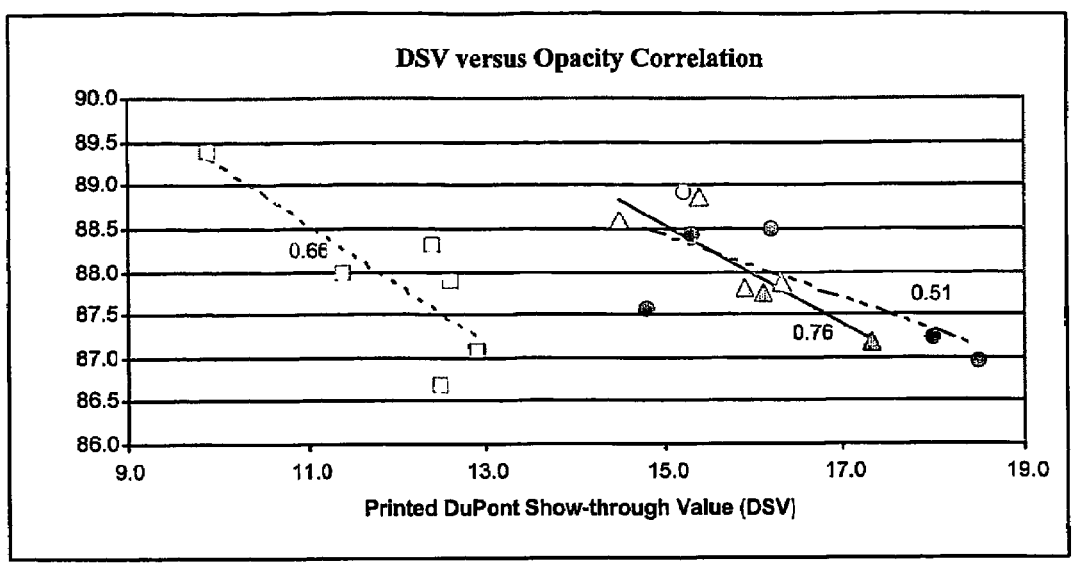
FIG. 9 is a plot showing the correlation of the output of the inventive method plotted against the opacity values produced by method of the TAPPI Standard T-425.

To quantify the showthrough of the printed image, a black image was printed on the samples on the reverse side from the side to be measured. The side to be measured had no printed image, (i.e., the side to be viewed was white). Each trend line in FIG. 9 represents one printing trial or one month's data. These trend lines vary, but appear to be generally consistent.

The plot of FIG. 9 illustrating the relationship between opacity (TAPPI T-425 method) and the DuPont Printed Show Through Value (DSV™) determined by the process of this invention was generated from the data in Table 1. The correlation between DSV™ and opacity is not very high, since the calculation is different and the size of the area being tested is much larger for DSV™ than for the T-425 method discussed below. The method of the present invention captures an image of a rectangular area of about 7 centimeters by 5 centimeters (2.58 inches by 2.0 inches), while the industry standard opacity measurement T-425 makes a single measurement using a 9.53 millimeter (0.375 inch) circular opening. Thus the present invention measures an area almost fifty times larger than the standard T-425 opacity measurement.

TABLE 1

| DSV ™ | Opacity |
|---|---|
| 11.40 | 88.00 |
| 12.60 | 87.91 |
| 12.90 | 87.10 |
| 12.50 | 86.69 |
| 12.40 | 88.31 |
| 9.90 | 89.39 |
| 17.30 | 87.16 |
| 15.40 | 88.87 |
| 16.10 | 87.74 |
| 15.90 | 87.8 |
| 16.30 | 87.85 |
| 14.50 | 88.58 |
| 14.80 | 87.56 |
| 18.50 | 86.96 |
| 16.20 | 88.51 |
| 18.00 | 87.24 |
| 15.30 | 88.43 |
| 15.20 | 88.91 |

In Table 1, the first six set of measurements are shown in FIG. 9 as square symbols, the next six set of measurements are shown in FIG. 9 as triangular symbols and the last six set of measurements are shown in FIG. 9 as circular symbols.

Measurement of opacity is in accordance with Technical Association of the Pulp and Paper Industry (TAPPI) standard T-425 om 01, entitled "Opacity of Paper (15/d Geometry, Illuminant A/2 Degrees, 89% Reflectance Backing and Paper Backing)": "the specimen opening shall be round with a diameter of 14.8±0.25 mm (0.584±0.010 in). The illuminated area shall be circular with a diameter of 9.53±0.38 mm (0.375±0.015 in) and centered in the specimen opening." In the experimental measurements, reported in Table 1, opacity was measured three times and the reported values represent the mean of these three measurements.

Figure 10:
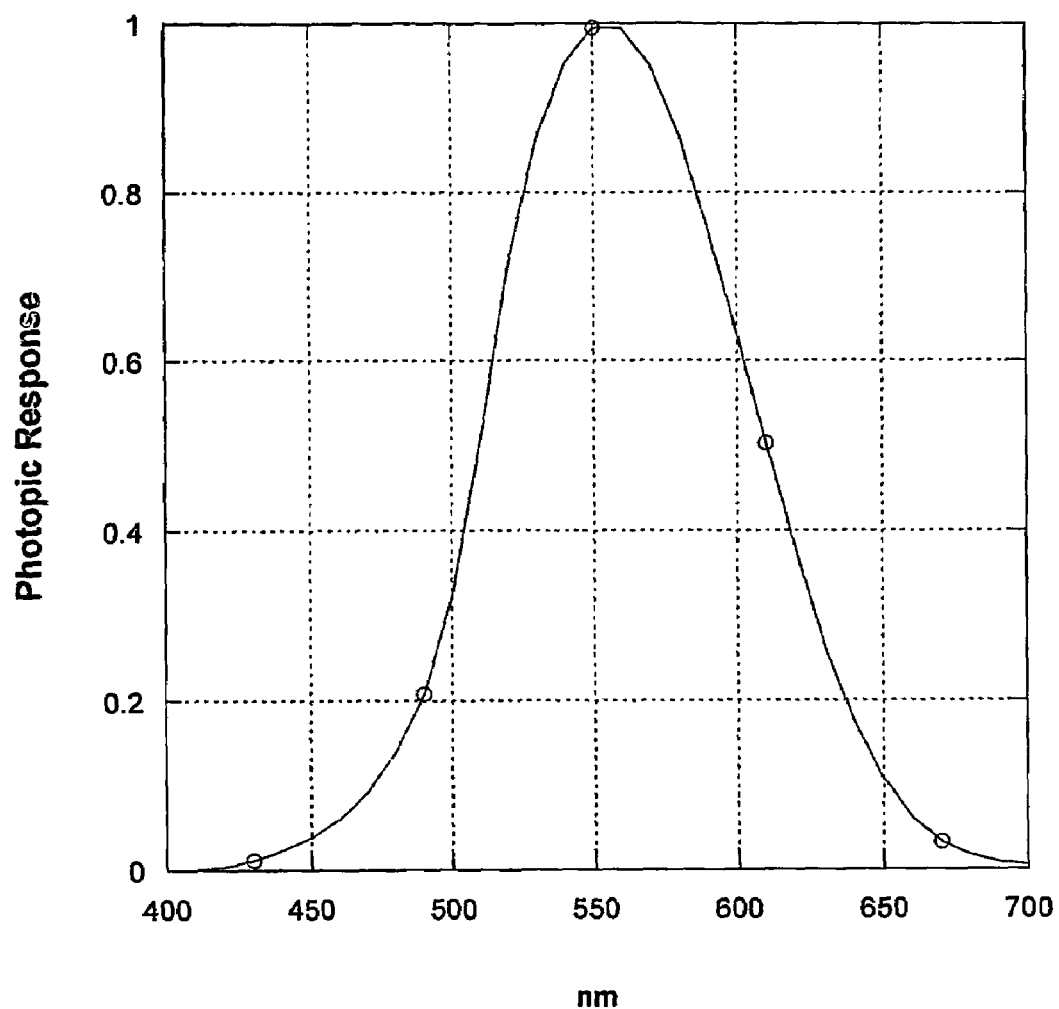
FIG. 10 is a plot showing the response of the photopic filter.

FIG. 10 shows a plot of the spectral response of the present invention (camera sensor, IR-cut filter at sensor (part of CCD array) and green filter). The green filter is chosen so that the total instrument spectral response closely matches the photopic response, i.e., the response of the human eye. Thus measurements made using the present invention should correlate well with observations of human observers.

The description of illustrative and preferred embodiments of the present invention is not intended to limit the scope of the invention. Various modifications, alternative constructions and equivalents may be employed without departing from the true spirit and scope of the appended claims.

What is claimed is:

1. A method for measuring the degree to which a printed image on a first side of a sheet is visible when illuminating and viewing a second side of the sheet, the method comprising:
    a) creating a calibration image of a reference object containing no image by illuminating the reference object at an initial illumination level;
    b) determining an average gray level of the reference object and adjusting the illumination level to achieve a predetermined average gray level;
    c) illuminating the sheet at an illumination level the same as the initial illumination level used to create the calibration image and creating an image of the sheet;
    d) measuring the ratios of the pixel intensities of the image of the sheet with the corresponding pixel intensities of the calibration image; and
    e) calculating a mean value of the ratios of the pixel intensities.

2. An image analysis method for characterizing the showthrough of a printed image on the reverse surface of a substantially planar sample object having a reflective front surface, by measuring the optical reflectance of the front surface with a lens and a photodetector array, the method comprising:
    (a) creating a frame-averaged dark current image representing the response of the photodetector array in the absence of light;
    (b) uniformly illuminating, with a diffuse light source, the front surface of a reference object, said reference object having no image on its reverse, and creating a calibration image of the reference object, comprising the steps of;
        (1) illuminating the front surface of the reference object with the diffuse light source, the output of the light source being set to an initial illumination output level;
        (2) creating a frame-averaged image of the front surface of the reference object;
        (3) determining the average gray level in the image of the reference object created in step(b)(2);
        (4) adjusting the illumination output level by adjusting the output of the light source and repeating steps (2) and (3) until the average light level reflected by the front surface of the reference object causes an average gray level in the image of step (2) to be within a predetermined range of a predetermined value within the dynamic range of the analog to digital converter, thereby establishing a predetermined illumination level;
        (5) creating a frame-averaged reference image of the front surface of the reference object;
        (6) creating a dark-current corrected calibration image of the reference object by subtracting the frame-averaged dark current image of step (a) from the frame-averaged reference image of step (5) on a pixel by pixel basis and storing the resulting image in the memory;
    (c) uniformly illuminating, with the diffuse light source at the predetermined illumination level, the front surface of a sample object having a printed image on the reverse surface;
    (d) creating a frame-averaged image of the front surface of the sample object;
    (e) creating a dark-current-corrected image of the front surface of the sample object by subtracting the frame-averaged dark current image of step (a) from the frame-averaged image of step (d) on a pixel by pixel basis and storing the resulting image in the memory; and
    (f) analyzing a dark-current-corrected frame-averaged image by calculating the ratio of the image of step (e) with the image of step (b)(6) on a pixel by pixel basis to quantify showthrough.

3. The method of claim 2, wherein the step (b)(2) of creating a frame-averaged image of the front surface of the reference object and step (d) of creating the frame-averaged image of the surface of the sample object each comprise the steps of:
    (1) imaging the light reflected from the front surface onto a photodetector array to create an electrical signal representative of the image;
    (2) digitizing the electrical signal using an analog to digital converter;
    (3) frame averaging the electrical signal a predetermined number of times; and
    (4) storing the frame-averaged digitized representation of the image as an array of picture elements in a memory.

4. The method of claim 2, wherein the analyzing step (f) comprises the steps of:

(1) calculating a ratio of the image of step (c) with the image of step (b)(6) on a pixel by pixel basis;
(2) calculating a mean value of the ratios of the pixels; and
(3) subtracting the mean value from the value 1.0 to create a quantitative representation of showthrough.

5. The method of claim 2, further comprising an optical filter in combination with the lens and the photodetector array, so that the overall spectral response of the combination is such that the image analysis method utilizes information in a predetermined spectral region.

6. The method of claim 5, further comprising the optical filter being positioned between the lens and the photodetector array, so that the overall spectral response of the combination is such that the image analysis method utilizes information in a spectral region that approximates the photopic response of the human eye.

7. The method of claim 2, wherein the illumination adjusting step (b)(4) is performed using a binary search method within a predetermined range of light levels.

8. The method of claim 2, wherein the illumination adjusting step (b)(4) is performed using a binary search method within the full range of light levels.

9. The method of claim 2, wherein a region of interest (ROI) in a field of view is selected before performing step (b) through (f).

10. The method of claim 2, wherein the reference object is comprised of a plurality of objects, each having no image on its reverse surface, stacked atop one another, such that a change in the number of objects in the stack results in no measurable difference in average gray level in the image of the reference object.

11. The method of claim 10, wherein the reference object is comprised of a plurality of sheets of paper.

12. The method of claim 2, wherein the sample object is a sheet of paper.

13. An apparatus for measuring the degree to which a printed image on a first side of a substantially planar sample object is visible when illuminating and viewing a second side of the substantially planar sample object, the apparatus comprising:
  a) a light tight enclosure comprising a sample object holder, an illuminating assembly for diffusely illuminating the sample object, and an imaging assembly,
  b) a computerized image processing assembly for controlling the illumination level of the sample object created by the illuminating assembly and for receiving images created by the imaging assembly and analyzing those images, wherein
    (1) the sample object holder comprises a support frame and a support platen for holding the sample object to be measured in a predetermined plane,
    (2) the illuminating assembly comprises:
      (i) a hemispherical reflector positioned adjacent the sample holder so that the predetermined plane corresponds to the equatorial plane of the hemispherical reflector, the hemispherical reflector having a diffusely reflecting interior surface and a polar opening for mounting the imaging assembly,
      (ii) a circular array of light sources positioned above the equatorial plane and arranged to illuminate the diffusely reflecting interior surface of the hemispherical reflector;
      (iii) a photodetector positioned adjacent the array of light sources and oriented to sense the level of light diffusely reflected from the interior surface of the hemispherical reflector;
    (3) the imaging assembly comprising:
      (i) a lens,
      (ii) a photodetector array, the lens focusing an image of the object onto the photodetector array, each photodetector in the array creating an electrical signal representative of the light reflected from the front surface of the object, the photodetector array being connected to the computerized image processing assembly.

14. The apparatus of claim 13, wherein each light source comprises a white light emitting diode.

15. The apparatus of claim 13, further comprising an optical filter in combination with the lens and the photodetector array, the filter having a spectral response such that the overall spectral response of the apparatus is a predetermined spectral response.

16. The apparatus of claim 15, further comprising an optical filter being positioned between the lens and the photodetector array, so that the overall spectral response of the apparatus approximates the photopic response of the human eye.

17. The apparatus of claim 13, wherein the interior surface of the hemispherical reflector has a substantially non-reflecting region adjacent the polar opening so that specular reflections from the object are not imaged by the imaging assembly.

18. The apparatus of claim 13, wherein the interior surface of the hemispherical reflector has a substantially non-reflecting region adjacent the polar opening corresponding to the area of the sample object being imaged.

* * * * *

UNITED STATES PATENT AND TRADEMARK OFFICE
CERTIFICATE OF CORRECTION

PATENT NO. : 7,620,211 B2
APPLICATION NO. : 10/549781
DATED : November 17, 2009
INVENTOR(S) : Browne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1094 days.

Signed and Sealed this

Twenty-sixth Day of October, 2010

David J. Kappos
*Director of the United States Patent and Trademark Office*